(12) United States Patent
Drost et al.

(10) Patent No.: US 9,127,928 B2
(45) Date of Patent: Sep. 8, 2015

(54) OBJECT LOCATION ACCOUNTING FOR PITCH, YAW AND ROLL OF DEVICE

(71) Applicant: General Electric Company, Schenectady, NY (US)

(72) Inventors: Eric Michael Drost, Flanders, NJ (US); Kevin Allan Bush, Marietta, NY (US); Edward Barrett Hubben, Skaneatles, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 379 days.

(21) Appl. No.: 13/677,486

(22) Filed: Nov. 15, 2012

(65) Prior Publication Data

US 2014/0132757 A1 May 15, 2014

(51) Int. Cl.
*H04N 7/18* (2006.01)
*G01B 11/00* (2006.01)
*G01N 21/88* (2006.01)
*G01N 21/954* (2006.01)

(52) U.S. Cl.
CPC .......... *G01B 11/002* (2013.01); *G01N 21/8851* (2013.01); *G01N 21/954* (2013.01)

(58) Field of Classification Search
USPC ............. 348/135, 137, 129, 143, 140, 84, 47, 348/50, 211.9, 284, 325, 330, 530, 605, 348/629, 776; 382/141, 149; 356/241.1, 356/456, 462, 611, 615
See application file for complete search history.

(56) References Cited

U.S. PATENT DOCUMENTS

| | | | | |
|---|---|---|---|---|
| 5,396,331 A | * | 3/1995 | Kitoh et al. ................... | 356/611 |
| 6,324,298 B1 | * | 11/2001 | O'Dell et al. ................. | 382/149 |
| 6,491,699 B1 | * | 12/2002 | Henderson et al. ........... | 606/130 |
| 6,931,149 B2 | * | 8/2005 | Hagene et al. ................ | 382/141 |
| 7,164,476 B2 | * | 1/2007 | Shima et al. ............... | 356/241.1 |
| 7,218,267 B1 | * | 5/2007 | Weil ................................ | 342/22 |
| 8,534,144 B2 | * | 9/2013 | Amir et al. ....................... | 73/865 |
| 2002/0065461 A1 | * | 5/2002 | Cosman ........................ | 600/426 |
| 2007/0184422 A1 | * | 8/2007 | Takahashi ..................... | 434/262 |
| 2007/0297752 A1 | * | 12/2007 | Soltysik .......................... | 386/46 |
| 2008/0058595 A1 | * | 3/2008 | Snoke et al. ................... | 600/114 |
| 2011/0137127 A1 | * | 6/2011 | Schwartz et al. ............. | 600/188 |
| 2012/0257042 A1 | * | 10/2012 | McKaigue et al. ............. | 348/84 |

* cited by examiner

*Primary Examiner* — Jefferey Harold
*Assistant Examiner* — Mustafizur Rahman
(74) *Attorney, Agent, or Firm* — Cooper Legal Group, LLC

(57) ABSTRACT

An inspection apparatus determines a location of a target object within a volume. The inspection apparatus includes a visual inspection device that determines a location of at least one reference point within the volume with respect to the visual inspection device. The visual inspection device further detects a location of the target object with respect to the visual inspection device. The visual inspection device utilizes a location of the target object with respect to the at least one reference point to determine a position of the target object within the volume. A method of locating the target object with the inspection apparatus is also provided.

20 Claims, 3 Drawing Sheets

US 9,127,928 B2

OBJECT LOCATION ACCOUNTING FOR PITCH, YAW AND ROLL OF DEVICE

BACKGROUND OF THE INVENTION

1. Field of the Invention

The present invention relates generally to an inspection instrument, and more particularly, to an inspection device for detecting a location of a target object within a component being inspected.

2. Discussion of the Prior Art

Inspection devices are known and used in many different applications. Inspection devices are used, for example, to inspect a volume and to detect/identify target objects within the volume. The volume can include, for example, a bound environment (e.g., pipes, tubes, turbines and their components, etc.) or an open environment (e.g., channel with at least one open side, etc.). The target objects within the volume may include corrosion, voids, inclusions, etc. on an interior surface (e.g., inner wall, etc.) of the volume. To accurately detect a position of the target object, the inspection devices uses a camera to observe the interior of the volume. The camera may be incorporated as part of a robotic crawler that is movable, though in further examples, the camera may include a movable probe tip. In general, the camera will move (e.g., translate, pan tilt, etc.) within the volume.

It is difficult to determine the precise location of the target object within the volume. Further, an orientation of the camera (e.g., pitch, yaw, roll) may not be known, thus making a determination of the target object's location even more difficult. Accordingly, it would be beneficial to provide an inspection device that determines the location of the target object by using the location of one or more reference points located within the volume. Further, it would be beneficial to account for the orientation of the camera (and/or the movable probe tip) during the location of the target object.

BRIEF DESCRIPTION OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect, an inspection apparatus for determining a location of a target object within a volume is provided. The inspection apparatus includes a visual inspection device configured to determine a location of at least one reference point within the volume with respect to the visual inspection device. The visual inspection device further detects a location of the target object with respect to the visual inspection device. The visual inspection device utilizes a location of the target object with respect to the at least one reference point to determine a position of the target object within the volume.

In accordance with another aspect, an inspection apparatus for determining a location of a target object within a volume is provided. The inspection apparatus includes a visual inspection device that determines a location of at least one reference point within the volume with respect to the visual inspection device. The visual inspection device further detects a distance from the visual inspection device to the target object. The visual inspection device utilizes the location of the at least one reference point and the distance of the target object with respect to the visual inspection device to determine a position of the target object within the volume.

In accordance with another aspect, a method of locating a target object with an inspection apparatus is provided. The method includes the step detecting the target object with a visual inspection device. The method further includes the step of measuring a distance to the target object from the visual inspection device. The method includes the step of determining a location of at least one reference point with respect to the visual inspection device. The method uses the location of the at least one reference point and the distance to the target object to determine a position of the target object.

BRIEF DESCRIPTION OF THE DRAWINGS

The foregoing and other aspects of the present invention will become apparent to those skilled in the art to which the present invention relates upon reading the following description with reference to the accompanying drawings, in which.

DETAILED DESCRIPTION OF THE INVENTION

Figure 1:
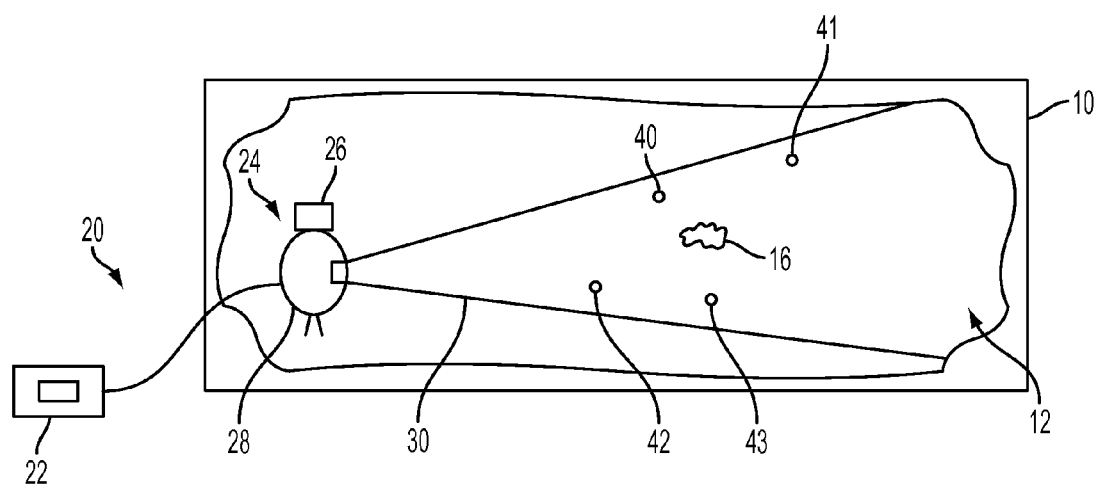
FIG. 1 is a schematic side view, partially torn open, of an example volume with an example inspection apparatus.

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

FIG. 1 illustrates a schematic side view of a partially torn open volume 10 and an example inspection apparatus 20 according to one aspect of the invention. The volume 10 includes both bound environments (as shown in FIG. 1, e.g., pipes, tubes, turbines and their components, etc.) and open environments (e.g., a channel with at least one open side, etc.). In short summary, the inspection apparatus 20 includes a visual inspection device 24 positioned within the volume 10. The visual inspection device 24 is used to detect a target object 16 (e.g., void, inclusion, crack, corrosion, etc.) on a wall of the volume 10. In one example, the visual inspection device 24 displays the interior of the volume 10 on a display screen, such that an operator identifies the presence of the target object 16. The visual inspection device 24 will then be used to detect at least one reference point within the volume 10. Based on an analysis of the location of the visual inspection device 24 with respect to the at least one reference point and to the target object 16, the relative location of the target object 16 within the volume 10 is determined.

The volume 10 is somewhat generically/schematically depicted in FIG. 1. In general, the volume 10 defines an interior portion 12 that is substantially hollow. In one example, the volume 10 defines an area that is relatively difficult to reach and/or is inaccessible to an operator. The volume 10 can include a number of different structures within the interior portion 12, including pipes, tubes, cylinders, conduits, or the like. In other examples, the volume 10 includes pipelines (for corrosion monitoring applications), air ducts and electrical conduits, steam lines/headers, large or small pressure vessels or tanks, etc. While FIG. 1 displays a bound environment (e.g., a hollow cylinder such as a pipe, tube, or the like), the volume 10 also includes an open environment, such as a channel with at least one open side or the like. The volume 10 may be larger or smaller than as shown, and may include one or more openings or the like to access the interior portion 12 of the volume 10. The volume 10 may also include bends, curves, undulations, etc., such that the volume 10 extends along either a linear or a non-linear axis. In one possible example, the volume 10 ranges from having an interior diameter of approximately 100 mm (~4 inches) to approximately 900 mm (~36 inches). Of course, other diameters are envisioned.

The volume 10 further includes the target object 16. The target object 16 is generically/schematically depicted in FIG. 1, as it is to be appreciated that the target object 16 includes a number of possible sizes, shapes, structures, and locations. For example, the target object 16 includes corrosion, voids, inclusions, defects, cracks, thicknesses, etc. located on an inner surface of the volume 10. The target object 16 includes any number of shapes and sizes, as FIG. 1 depicts only one example target object 16. In other examples, the target object 16 is not limited to the single target object shown in FIG. 1, and instead includes a plurality of target objects. The target object 16 may be located at a variety of locations within the interior portion 12. For example, the target object 16 could be located along an inner wall of the volume 10. In other examples, the target object 16 is located within one of the walls of the volume 10. In yet another example, the target object 16 is not limited to being located on a wall of the volume 10. Rather, the target object 16 is located on a structure positioned within the volume 10.

Turning now to the inspection apparatus 20, the inspection apparatus 20 includes a control unit 22. The control unit 22 is generically/schematically depicted, as the control unit 22 may include a number of different configurations. In one example, the control unit 22 is operatively attached to the visual inspection device 24 by means of a wire (as shown). Of course, in other examples, the control unit 22 is in wireless communication with the visual inspection device 24. The control unit 22 may be located at an exterior of the volume 10, as shown, though in further examples, the control unit 22 could instead be positioned at least partially within the interior portion 12 of the volume 10. Due to the potential for use in a variety of environments (e.g., high/low temperatures, high/low humidity, presence/absence of moisture), the control unit 22 is designed to be relatively durable and resistant to environmental effects.

The control unit 22 sends and receives information (e.g., data, control instructions, etc.) to/from the visual inspection device 24 through the wire (or wirelessly). This information can be related to characteristics of the volume 10, characteristics of a field of view of the visual inspection device 24, or the like. In further examples, the control unit 22 sends control instructions to the visual inspection device 24 to cause the visual inspection device 24 to move (e.g., translate within the volume 10, pan, tilt, rotate, zoom, etc.). The control unit 22 can include circuits, processors, running programs, memories, computers, power supplies, ultrasound contents, or the like. In one example, the control unit 22 includes a user interface, display, and/or other devices for allowing a user to control the inspection device. The display will display the interior portion 12 of the volume 10 to allow an operator to identify the presence of the target object 16.

Turning to the visual inspection device 24 of the inspection apparatus 20, the visual inspection device 24 is positioned within the interior portion 12 of the volume 10. It is to be appreciated that the visual inspection device 24 is somewhat generically/schematically depicted, as the visual inspection device 24 includes a number of different configurations. In one example, the visual inspection device 24 is movable within the interior portion 12. In such an example, the visual inspection device 24 includes a robotic crawler that has a drive unit (e.g., wheels, tires, continuous tracks, etc.) and related drive components such that the control unit 22 can control movement of the visual inspection device 24 (e.g., robotic crawler). In another possible example, the visual inspection device 24 could include a video boroscope that has a movable probe tip. In general, however, the visual inspection device 24 will move within the volume 10 and, once the target object 16 is identified, the visual inspection device 24 will stop moving. At this point, the visual inspection device 24 will pan/tilt/zoom, etc. while remaining stationary so as to identify the target object 16 and the surrounding environment.

The visual inspection device 24 includes a lighting apparatus 26. The lighting apparatus 26 includes an electric-powered light source, such as a flash light, bulb, or similar device. The lighting apparatus 26 is positioned at an upper portion of the visual inspection device 24, but in further examples, could be provided at any location within the visual inspection device 24. Due to the potential for lack of light within the interior portion 12 of the volume 10, the lighting apparatus 26 can be selectively turned on and off to illuminate the interior portion 12. In one example, the lighting apparatus 26 is controllable by the control unit 22, though in further examples, the lighting apparatus 26 may automatically turn on/off by detecting the presence/absence of light.

The visual inspection device 24 further includes a camera 28. The camera 28 has a field of view 30 directed towards the interior portion 12 of the volume 10. The camera 28 is movable, such that the field of view 30 can be directed at a variety of locations within the interior portion 12, such as axially along the volume 10, transverse to an axis along which the volume 10 extends, up or down, etc. In one example, the camera 28 includes a pan-tilt-zoom (PTZ) camera attached to the robotic crawler. In another example, the camera 28 is incorporated as part of a boroscope assembly having a movable probe tip.

The camera 28 is somewhat generically/schematically depicted, as the camera 28 includes a number of different constructions. For example, the camera 28 can include any number of image in-taking devices for capturing images and/or video. In one example, the camera 28 includes a rangefinder camera having a range-finding focusing mechanism. The camera 28 therefore measures a subject distance from the visual inspection device 24 to a predetermined point. The camera 28 is not limited to the structure shown in FIG. 1, and instead could include a number of different constructions. In other examples, the camera 28 could include a video probe and/or an elongate image in-taking device. In general, the camera 28 will be small enough so as to permit insertion of the camera 28 into the interior portion 12 of the volume 10 and, in some examples, allow for movement of the camera 28 therein. The camera 28 can transmit information (e.g., images, distances, etc.) from the interior portion 12 to the control unit 22.

The camera 28 can detect the presence and/or location of the target object 16 within the volume 10. The camera 28 detects the target object 16 in any number of ways, such as by visually locating the target object 16, transmitting/receiving sound waves within the interior portion 12, or the like. In one possible example, the camera 28 will in-take images within the volume 10, and display these images on a screen, monitor, etc., such that an operator can visually identify the target object 16. Once the target object 16 is located/detected, the visual inspection device 24 will stop moving and the relative location of the target object 16 within the volume 10 is determinable. Further, to accommodate for any pitch, yaw, or roll of the visual inspection device 24, an orientation of the visual inspection device 24 will also be determined.

To determine the relative location of the target object 16, the visual inspection device 24 will first determine a location of at least one reference point within the volume 10. In one example, the reference points are chosen at random within the volume 10. In other examples, the reference points may include target objects or markers whose location within the volume 10 is already known. In such an example, the location of the reference points within the volume 10 may be known, such as by knowing the axial location along the volume 10, circumferential location around the volume 10, etc.

As shown in FIG. 1, the at least one reference point can, in one particular example, include four reference points: a first reference point 40, a second reference point 41, a third reference point 42, and a fourth reference point 43. The reference points 40-43 are located on a wall, such as an inner wall, of the volume 10 within the field of view 30 of the camera 28. In one example, the reference points 40-43 can be located in proximity to the target object 16. It is to be appreciated that FIG. 1 depicts only one of many possible locations of the reference points 40-43. The reference points 40-43 are of course not limited to the shown locations, and instead could be found at other locations, including closer to or farther from the target object 16.

Figure 2:
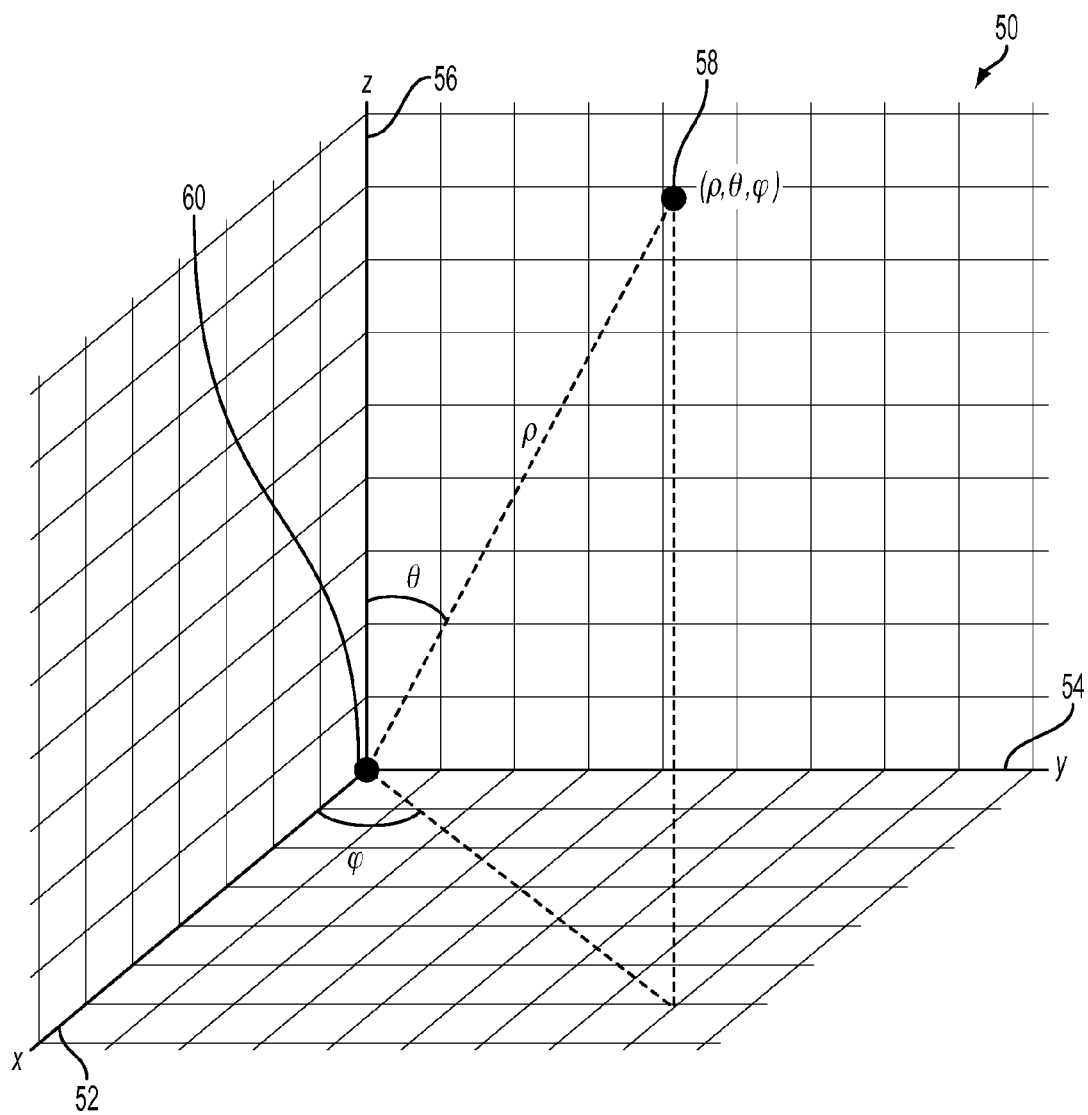
FIG. 2 is a schematic perspective view of a three-dimensional plot depicting a location of the example visual inspection device with respect to reference points of the volume.

Turning now to FIG. 2, the operation of determining the relative location of the target object 16 with respect to the reference points 40-43 will be fully described. FIG. 2 shows a three-dimensional plot 50 depicting a location of the example visual inspection device 24 (at device location 60) with respect to one of the reference points 40-43 (at representative point 58). The three-dimensional plot 50 can be associated with the control unit 22, in one example. For instance, the control unit 22 can display the three-dimensional plot 50 on a display screen, or the like.

It is to be appreciated that FIG. 2 does not depict all of the features shown in FIG. 1, such as the volume 10, the control unit 22, etc. Rather, for illustrative purposes, FIG. 2 is merely intended to show the location of the visual inspection device 24 with respect to one of the reference points 40-43 in a three-dimensional spherical coordinate system.

The three-dimensional plot 50 includes three axes for plotting locations of the visual inspection device 24 and reference points 40-43. The three-dimensional plot 50 includes an x axis 52, a y-axis 54, and a z-axis 56. In the shown example, the representative point 58 is plotted on the three-dimensional plot 50. The representative point 58 represents one of the reference points shown in FIG. 1. For example, the representative point 58 can represent the first reference point 40, second reference point 41, third reference point 42, or fourth reference point 43. It is to be appreciated that only one representative point 58 is depicted in FIG. 2 for ease of illustration. However, in operation, the three-dimensional plot 50 will include separate representative points for each of the four reference points 40-43, such that there would be four representative points in such an example. Additionally, the representative point 58 shown in FIG. 2 is somewhat generically placed, as the reference points 40-43 could be plotted at a variety of different locations within the three-dimensional plot 50. Indeed, the other three reference points will be placed at differing locations from the shown representative point 58.

The three-dimensional plot 50 further includes the device location 60. In this example, the device location 60 is depicted at an origin of the x-axis 52, y-axis 54, and z-axis 56 (e.g., location at which the x-axis 52, y-axis 54, and z-axis 56 intersect). The device location 60 represents the location of the visual inspection device 24. It is to be appreciated that FIG. 2 does not show the visual inspection device 24 but, rather, only shows the location of the visual inspection device 24 for illustrative purposes. Indeed, the device location 60 of the visual inspection device 24 is depicted somewhat generically/schematically as a point for ease of illustration. As such, the device location 60 represents the location of the visual inspection device 24 with respect to the reference points 40-43. By being placed at the origin of the three-dimensional plot 50, the device location 60 is located at point (0, 0, 0). The representative point 58 is therefore plotted with respect to the device location 60. The device location 60 is relatively stationary within the volume 10 once the target object 16 is located, but for panning/tilting/zooming of the camera 28.

The three-dimensional plot 50 represents the relative location of the reference points 40-43 (i.e., shown as representative point 58) including the target object 16 with respect to the device location 60. In the shown example, the representative point 58 is represented as a point with coordinates (e.g., $\rho$, $\Theta$, $\phi$). Rho $\rho$ (shown as a hatched line) represents a radial distance ("distance") from the device location 60 to the representative point 58. Phi $\phi$ represents a zenith angle from the positive x-axis 56 to the representative point 58. Theta $\theta$ represents an azimuth angle from the positive z-axis to the representative point 58. Accordingly, rotating the visual inspection device 24 counterclockwise will increase phi $\phi$. Rotating the visual inspection device 24 downwards will increase theta $\theta$. Moving the visual inspection device 24 away from the reference points 40-43 will increase the distance rho $\rho$.

First, the relative locations of the reference points 40-43 with respect to the visual inspection device 24 will be determined. The visual inspection device 24 is assumed to be located at (0,0,0), with the visual inspection device 24 oriented vertically (i.e., along the z-axis 56) and facing the x-axis 52, with the distance (rho $\rho$) being zero. The device location 60 of the visual inspection device 24 is represented as (X, Y, Z)$_{PT}$ in the following equations. As is generally known, the equations to convert between Cartesian and polar coordinates are represented in equations (1) to (3).

$$X = \rho \sin(\theta)\cos(\phi) \tag{1}$$

$$Y = \rho \sin(\theta)\sin(\phi) \tag{2}$$

$$Z = \rho \cos(\theta) \tag{3}$$

Next, data pertaining to the location of the reference points 40-43 is determinable. In particular, the distance (rho $\rho$) from the visual inspection device 24 to each of the reference points 40-43 is determinable with the rangefinder. Likewise, the angles theta $\theta$ and phi $\phi$ can be measured from the device location 60 for the representative point 58 (e.g., each of the reference points 40-43). With the location of the reference points 40-43 stored, the visual inspection device 24 can then determine the location of the target object 16 with respect to the visual inspection device 24 and store this information.

With the location data of the reference points 40-43 and target object 16 with respect to the device location 60 now determined, a process of quadlateration is used to determine the location of the visual inspection device 24. In particular, the following equations are presented for using this information to determine the device location 60. Initially, a distance formula shown in equation (4) is derived from the Law of Cosines.

$$\rho^2 = X_{PT}^2 + Y_{PT}^2 + Z_{PT}^2 + X^2 + Y^2 + Z^2 - 2(X, Y, Z) * (X_{PT}, Y_{PT}, Z_{PT}) \quad (4)$$

Next, four simultaneous distance equations (shown below as equations (5) to (8)) are set up to prepare a linear system of equations. Each of the distance equations relate to a distance between the device location 60 and one of the reference points 40-43. For example, $\rho_{40}$ represents a distance from the device location 60 to the first reference point 40. Similarly, $X_{40}$, $Y_{40}$, and $Z_{40}$ represent the X, Y, and Z coordinates of the first reference point 40. Likewise, distances and XYZ coordinates for the other reference points 41-43 are similarly represented.

$$\rho_{40}^2 = X_{PT}^2 + Y_{PT}^2 + Z_{PT}^2 + X_{40}^2 + Y_{40}^2 + Z_{40}^2 - 2(X_{40}, Y_{40}, Z_{40}) * (X_{PT}, Y_{PT}, Z_{PT}) \quad (5)$$

$$\rho_{41}^2 = X_{PT}^2 + Y_{PT}^2 + Z_{PT}^2 + X_{41}^2 + Y_{41}^2 + Z_{41}^2 - 2(X_{41}, Y_{41}, Z_{41}) * (X_{PT}, Y_{PT}, Z_{PT}) \quad (6)$$

$$\rho_{42}^2 = X_{PT}^2 + Y_{PT}^2 + Z_{PT}^2 + X_{42}^2 + Y_{42}^2 + Z_{42}^2 - 2(X_{42}, Y_{42}, Z_{42}) * (X_{PT}, Y_{PT}, Z_{PT}) \quad (7)$$

$$\rho_{43}^2 = X_{PT}^2 + Y_{PT}^2 + Z_{PT}^2 + X_{43}^2 + Y_{43}^2 + Z_{43}^2 - 2(X_{43}, Y_{43}, Z_{43}) * (X_{PT}, Y_{PT}, Z_{PT}) \quad (8)$$

Using these four distance equations (equations (5) to (8)), values for $(X, Y, Z)_{PT}$ will be substituted into each equation such that the dot product equates to a constant. In particular, rearranging the first and second distance equations (equations (5) and (6)) will produce the following:

$$X_{PT}^2 + Y_{PT}^2 + Z_{PT}^2 = \rho_{40}^2 - X_{40}^2 - Y_{40}^2 - Z_{40}^2 + 2(X_{40}, Y_{40}, Z_{40}) * (X_{PT}, Y_{PT}, Z_{PT}) \quad (9)$$

$$X_{PT}^2 + Y_{PT}^2 + Z_{PT}^2 = \rho_{41}^2 - X_{41}^2 - Y_{41}^2 - Z_{41}^2 + 2(X_{41}, Y_{41}, Z_{41}) * (X_{PT}, Y_{PT}, Z_{PT}) \quad (10)$$

Combining these two equations will produce:

$$\rho_{41}^2 - X_{41}^2 - Y_{41}^2 - Z_{41}^2 + 2(X_{41}, Y_{41}, Z_{41}) * (X_{PT}, Y_{PT}, Z_{PT}) = \rho_{40}^2 - X_{40}^2 - Y_{40}^2 - Z_{40}^2 + 2(X_{40}, Y_{40}, Z_{40}) * (X_{PT}, Y_{PT}, Z_{PT}) \quad (11)$$

This equation (equation (11)) can be rearranged to show:

$$2(X_{41}, Y_{41}, Z_{41}) * (X_{PT}, Y_{PT}, Z_{PT}) - 2(X_{40}, Y_{40}, Z_{40}) * (X_{PT}, Y_{PT}, Z_{PT}) = \rho_{40}^2 - \rho_{41}^2 + X_{41}^2 + Y_{41}^2 + Z_{41}^2 - X_{40}^2 - Y_{40}^2 - Z_{40}^2 \quad (12)$$

$$(X_{41}, Y_{41}, Z_{41}) * (X_{PT}, Y_{PT}, Z_{PT}) - (X_{40}, Y_{40}, Z_{40}) * (X_{PT}, Y_{PT}, Z_{PT}) = \frac{\rho_{40}^2 - \rho_{41}^2 + X_{41}^2 + Y_{41}^2 + Z_{41}^2 - X_{40}^2 - Y_{40}^2 - Z_{40}^2}{2} \quad (13)$$

Finally, equation (13) can be rewritten as:

$$(X_{41} - X_{40}, Y_{41} - Y_{40}, Z_{41} - Z_{40}) * (X_{PT}, Y_{PT}, Z_{PT}) = \frac{\rho_{40}^2 - \rho_{41}^2 + X_{41}^2 + Y_{41}^2 + Z_{41}^2 - X_{40}^2 - Y_{40}^2 - Z_{40}^2}{2} \quad (14)$$

Similar equations can be obtained for the second reference point 41 and third reference point 42 (shown in equation (15) below), for the first reference point 40 and the third reference point 42 (shown in equation (16) below), and for the first reference point 40 and the fourth reference point 43 (shown in equation (17) below).

$$(X_{42} - X_{41}, Y_{42} - Y_{41}, Z_{42} - Z_{41}) * (X_{PT}, Y_{PT}, Z_{PT}) = \frac{\rho_{41}^2 - \rho_{42}^2 + X_{42}^2 + Y_{42}^2 + Z_{42}^2 - X_{41}^2 - Y_{41}^2 - Z_{41}^2}{2} \quad (15)$$

$$(X_{40} - X_{42}, Y_{40} - Y_{42}, Z_{40} - Z_{42}) * (X_{PT}, Y_{PT}, Z_{PT}) = \frac{\rho_{42}^2 - \rho_{40}^2 + X_{40}^2 + Y_{40}^2 + Z_{40}^2 - X_{42}^2 - Y_{42}^2 - Z_{42}^2}{2} \quad (16)$$

$$(X_{40} - X_{43}, Y_{40} - Y_{43}, Z_{40} - Z_{43}) * (X_{PT}, Y_{PT}, Z_{PT}) = \frac{\rho_{43}^2 - \rho_{40}^2 + X_{40}^2 + Y_{40}^2 + Z_{40}^2 - X_{43}^2 - Y_{43}^2 - Z_{43}^2}{2} \quad (17)$$

Each of equations (14) to (17) can be rewritten in matrix form to calculate the $(X, Y, Z)_{PT}$ coordinates. For example, a linear system including a 4×3 coefficient matrix, a 3×1 variable matrix, and a 4×1 solution matrix are formed from the above equations to find a least square solution.

$$\begin{bmatrix} X_{41} - X_{40} & Y_{41} - Y_{40} & Z_{41} - Z_{40} \\ X_{42} - X_{41} & Y_{42} - Y_{41} & Z_{42} - Z_{41} \\ X_{40} - X_{42} & Y_{40} - Y_{42} & Z_{40} - Z_{42} \\ X_{40} - X_{43} & Y_{40} - Y_{43} & Z_{40} - Z_{43} \end{bmatrix} \begin{bmatrix} X_{PT} \\ Y_{PT} \\ Z_{PT} \end{bmatrix} = \quad (18)$$

$$\begin{bmatrix} \frac{\rho_{40}^2 - \rho_{41}^2 + X_{41}^2 + Y_{41}^2 + Z_{41}^2 - X_{40}^2 - Y_{40}^2 - Z_{40}^2}{2} \\ \frac{\rho_{41}^2 - \rho_{42}^2 + X_{42}^2 + Y_{42}^2 + Z_{42}^2 - X_{41}^2 - Y_{41}^2 - Z_{41}^2}{2} \\ \frac{\rho_{42}^2 - \rho_{40}^2 + X_{40}^2 + Y_{40}^2 + Z_{40}^2 - X_{42}^2 - Y_{42}^2 - Z_{42}^2}{2} \\ \frac{\rho_{43}^2 - \rho_{40}^2 + X_{40}^2 + Y_{40}^2 + Z_{40}^2 - X_{43}^2 - Y_{43}^2 - Z_{43}^2}{2} \end{bmatrix}$$

As is generally known, the formula for the least squares solution of the linear system described by $Ax=b$ is $A^T A x = A^T b$. Accordingly, values pertaining to the four reference points 40-43 (e.g., radial distance $\rho$, zenith angle $\phi$, azimuth angle $\theta$) with respect to the device location 60 can be inputted into the above matrix to determine the initial position of the visual inspection device 24 with respect to the reference points 40-43. At this point, the relative position of the device location 60 with respect to the reference points 40-43 is known.

Next, using the relative positions of the device location 60 with respect to the reference points 40-43, the orientation of the visual inspection device 24 can be determined. The orientation of the visual inspection device 24 can include pitch, yaw, and/or roll of the visual inspection device 24. The pitch of the visual inspection device 24 refers to a vertical force applied at a distance forward or backward from a center of gravity of the visual inspection device 24, such that the visual inspection device 24 will pitch upwards or downwards. In one example, pitch includes rotation about the y-axis 54. A roll of the visual inspection device 24 can include a rotation of the visual inspection device 24 about the x-axis 52. A yaw of the visual inspection device 24 can include a rotation of the visual inspection device 24 about the z-axis 56. The orientation of the visual inspection device 24 is affected in any number of ways, such as by having an uneven terrain within the volume 10 or the like.

To determine the orientation for the visual inspection device 24, origin perspective coordinates are introduced. In one example, the origin perspective coordinates are provided as variables $(X_0, Y_0, Z_0)$ for the location of each of the reference points 40-43 and for the target object 16. As is generally known, the equations to convert between Cartesian and polar coordinates are shown in equations (1) to (3).

$$X_0 = \rho \sin(\theta)\cos(\phi) \quad (19)$$

$$Y_0 = \rho \sin(\theta)\sin(\phi) \quad (20)$$

$$Z_0 = \rho \cos(\theta) \quad (21)$$

Next, the origin perspective coordinates are multiplied by a transformation (or rotation) matrix, such as a 3×3 transformation matrix. The 3×3 transformation matrix exists such that when multiplied by the origin perspective coordinates of a point, the coordinates of the distance to the target object 16 from the visual inspection device 24 are produced. In particular, when the 3×3 transformation matrix (shown below in equation (22) with values represented by $R_{11}$, $R_{12}$, R13, etc.) is multiplied by the origin perspective coordinates (which is also a 3×3 matrix with coordinates $X_0$, $Y_0$, $Z_0$), the coordinates of the distance to the target object 16 from the visual inspection device 24 are produced. These coordinates can include, for example, the original coordinates. The relative position of the device location 60 with respect to the reference points 40-43 can be compared to the relative position of the device location 60 with respect to the target object 16 to determine the actual location of the target object 16 within the volume 10.

$$\begin{bmatrix} R_{11} & R_{12} & R_{13} \\ R_{21} & R_{22} & R_{23} \\ R_{31} & R_{32} & R_{33} \end{bmatrix} \begin{bmatrix} X_0 \\ Y_0 \\ Z_0 \end{bmatrix} = \begin{bmatrix} X \\ Y \\ Z \end{bmatrix} \quad (22)$$

Next, equation (23) is used to solve for the values of the transformation matrix. In particular, as shown in formula (23) below, the original coordinates (described above with respect to equation (18)) can be subtracted by PT coordinates and augmented with one of origin perspective coordinates for three known points:

$$\begin{bmatrix} X_{40-PT} & Y_{40-PT} & Z_{40-PT} & X_{40_0} & Y_{40_0} & Z_{40_0} \\ X_{41-PT} & Y_{41-PT} & Z_{41-PT} & X_{41_0} & Y_{41_0} & Z_{41_0} \\ X_{42-PT} & Y_{42-PT} & Z_{42-PT} & X_{42_0} & Y_{42_0} & Z_{42_0} \end{bmatrix} \quad (23)$$

Next, the real coordinate matrix is reduced with Gauss-Jordan elimination. As such, the augmented matrix reduces to a transformation matrix that converts from origin perspective coordinates to coordinates of distance to the target object 16 from the visual inspection device 24.

$$\begin{bmatrix} 1 & 0 & 0 & R_{11} & R_{12} & R_{13} \\ 0 & 1 & 0 & R_{21} & R_{22} & R_{23} \\ 0 & 0 & 1 & R_{31} & R_{32} & R_{33} \end{bmatrix} \quad (24)$$

Once the original coordinates have been reduced into an identity matrix, the origin perspective coordinates are thus transformed into the transformation matrix's values, as denoted in formula (24). Finally, the transformation matrix is multiplied with the origin perspective coordinates of the location of the target object 16 and added with (X, Y, Z)$_{PT}$ to determine the real coordinates of the target object 16 location. In particular, multiplying the transformation matrix with the origin perspective coordinates of the location of the target object 16 will yield the coordinates of the distance to the target object 16 from the visual inspection device 24. These coordinates (i.e., distance to the target object 16 from the visual inspection device 24) are added to the location of the visual inspection device 24 (e.g., (X, Y, Z)$_{PT}$) to determine the real coordinates of the location of the target object 16.

$$\begin{bmatrix} R_{11} & R_{12} & R_{13} \\ R_{21} & R_{22} & R_{23} \\ R_{31} & R_{32} & R_{33} \end{bmatrix} \begin{bmatrix} X_{16_0} \\ Y_{16_0} \\ Z_{16_0} \end{bmatrix} + \begin{bmatrix} X_{PT} \\ Y_{PT} \\ Z_{PT} \end{bmatrix} = \begin{bmatrix} X_{16} \\ Y_{16} \\ Z_{16} \end{bmatrix} \quad (25)$$

Accordingly, as represented in equation (25), the coordinates of the distance to the target object 16 from the visual inspection device 24 plus (X, Y, Z)$_{PT}$ are equal to the real coordinates of the location of the target object 16, represented by ($X_{16}$, $Y_{16}$, $Z_{16}$).

The aforementioned description allows for an accurate determination of the target object 16 within the volume 10. In particular, during inspection, the location of the target object 16 relative to a known marker/target object (e.g., reference points 40-43) will be used to determine the target object's location. Further, the aforementioned description allows for a user/operator to take into account the relative location, orientation, and/or position of the visual inspection device 24 being used to locate the target object 16.

Figure 3:
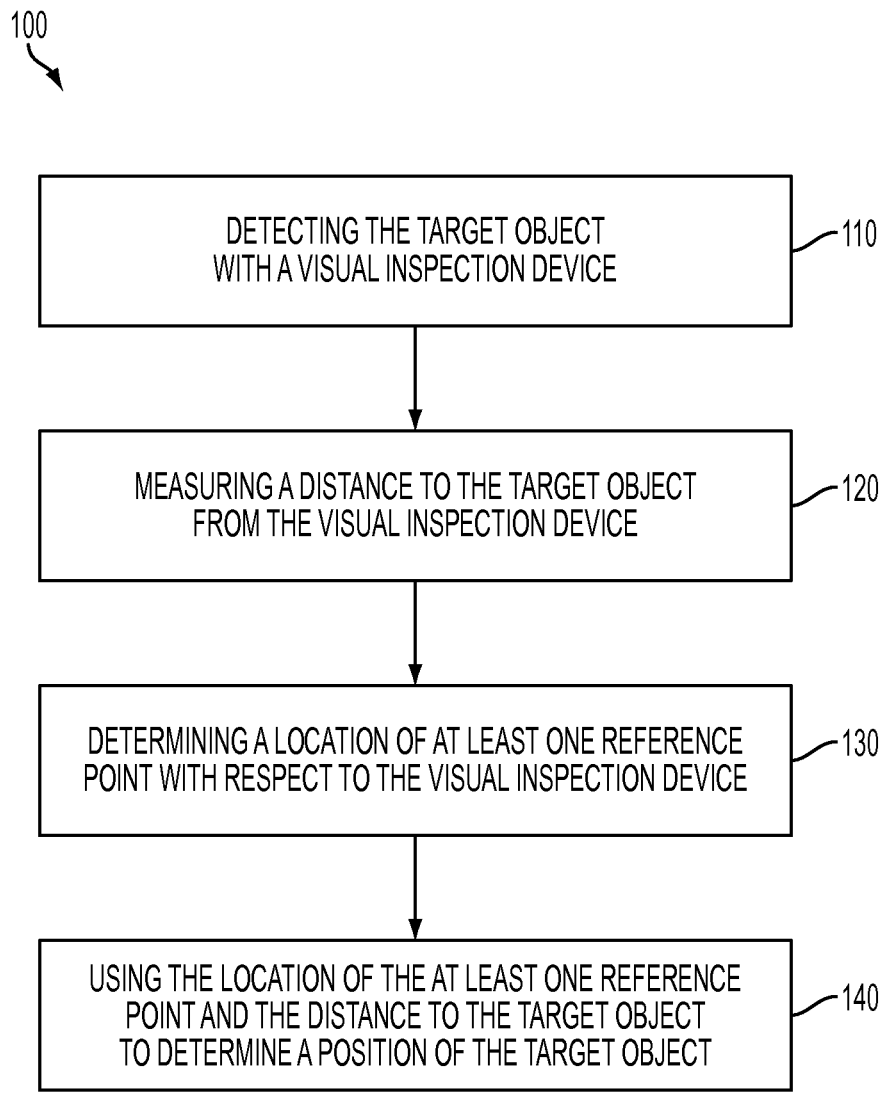
FIG. 3 is a flow diagram of an example method of locating a target object with the example inspection apparatus.

Turning now to FIG. 3, an example method 100 of locating the target object 16 with the inspection apparatus 20 is shown. The method can be performed in association with the example volume 10 and inspection apparatus 20 shown in FIG. 1. The method can also be performed in association with the example three-dimensional plot 50 shown in FIG. 2.

The method 100 includes a step 110 of detecting the target object 16 with the visual inspection device 24. In particular, as shown in FIG. 1, the camera 28 of the visual inspection device 24 will direct the field of view 30 into the interior portion 12 of the volume 10. The camera 28 can detect the target object 16, such as by displaying the target object 16 on a monitor, display screen, etc. for a user to identify. The target object 16 may be located on an inner wall or structure within the volume 10. The target object 16 includes, for example, voids, inclusions, cracks, corrosion, etc.

The method 100 further includes a step 120 of measuring the distance to the target object 16 from the visual inspection device 24. In particular, the camera 28 may include a rangefinder having a range-finding focusing mechanism, or other similar distance detection devices. The camera 28 will focus on the target object 16 and can determine the distance from the visual inspection device 24 to the target object 16.

The method 100 also includes a step 130 of determining the location of at least one reference point with respect to the visual inspection device 24. In particular, the camera 28 of the visual inspection device 24 will focus on the four reference points 40-43 within the volume 10. Using the rangefinder (e.g., range-finding focusing mechanism, etc.), the camera 28 will determine the distance to each of the four reference points 40-43 from the visual inspection device 24.

The method 100 further includes a step 140 of using the location of the at least one reference point and the distance to the target object 16 to determine the position of the target object 16. In particular, the camera 28 will determine the relative positions of each of the reference points 40-43 with respect to the visual inspection device 24. These relative locations, along with the distance to the target object 16 from the visual inspection device 24, will be stored. Next, using the aforementioned equations (equations (1) to (18)), the values pertaining to the four reference points 40-43 (e.g., radial distance ρ, zenith angle φ, azimuth angle θ) with respect to the device location 60 are inputted into the equations to determine the initial position of the visual inspection device 24 with respect to the reference points 40-43. Following this, equations (19) to (25) are used to determine the real coordinates of the location of the target object 16.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. An inspection apparatus for determining a location of a target object within a volume, the inspection apparatus including:
   a visual inspection device configured to determine a location of at least one reference point at a distance from the visual inspection device within the volume with respect to the visual inspection device, the visual inspection device further being configured to detect a location of the target object at a distance from the visual inspection device and with respect to the visual inspection device;
   wherein the visual inspection device utilizes a location of the target object with respect to the at least one reference point to determine a position of the target object within the volume.

2. The inspection apparatus of claim 1, wherein the visual inspection device is movable relative to the reference point and relative to the target object.

3. The inspection apparatus of claim 2, wherein the visual inspection device is movable by tilting along a Y-axis.

4. The inspection apparatus of claim 2, wherein the visual inspection device is movable by panning along an X-axis.

5. The inspection apparatus of claim 1, wherein the visual inspection device includes a camera.

6. The inspection apparatus of claim 1, wherein the visual inspection device includes a rangefinder for determining a distance from the visual inspection device to the at least one reference point.

7. The inspection apparatus of claim 6, wherein the rangefinder is configured to determine a distance from the visual inspection device to the target object.

8. The inspection apparatus of claim 1, wherein the at least one reference point within the volume includes four reference points.

9. The inspection apparatus of claim 8, wherein the visual inspection device utilizes the location of the four reference points to determine an orientation of the visual inspection device.

10. An inspection apparatus for determining a location of a target object within a volume, the inspection apparatus including:
    a visual inspection device configured to determine a location of at least one reference point at a distance from the visual inspection device within the volume with respect to the visual inspection device, the visual inspection device further being configured to detect a distance from the visual inspection device to the target object;
    wherein the visual inspection device utilizes the location of the at least one reference point and the distance of the target object with respect to the visual inspection device to determine a position of the target object within the volume.

11. The inspection apparatus of claim 10, wherein the visual inspection device is movable.

12. The inspection apparatus of claim 11, wherein the visual inspection device is movable by tilting along a Y-axis.

13. The inspection apparatus of claim 12, wherein the visual inspection device is movable by panning along an X-axis.

14. The inspection apparatus of claim 10, wherein the visual inspection device includes a camera.

15. The inspection apparatus of claim 10, wherein the visual inspection device includes a rangefinder for determining a distance from the visual inspection device to the at least one reference point.

16. The inspection apparatus of claim 15, wherein the rangefinder is configured to determine a distance from the visual inspection device to the target object.

17. A method of locating a target object with an inspection apparatus, the method including the steps of:
    detecting the target object at a distance from the visual inspection device and with a visual inspection device;
    measuring the distance to the target object from the visual inspection device;
    determining a location of at least one reference point at a distance from the visual inspection device and with respect to the visual inspection device; and
    using the location of the at least one reference point and the distance to the target object to determine a position of the target object.

18. The method of claim 17, wherein the at least one reference point includes four reference points.

19. The method of claim 18, further including the step of measuring the distance to each of the four reference points from the visual inspection device.

20. The method of claim 17, further including the step of plotting the location of the at least one reference point with respect to the visual inspection device on a three-dimensional plot.

* * * * *